United States Patent
Lu

(10) Patent No.: US 8,130,094 B2
(45) Date of Patent: Mar. 6, 2012

(54) MISTAKE-PROOF MONITORING METHOD OF BEDRIDDEN CARE SYSTEM

(75) Inventor: Lee-Tsan Lu, Taipei (TW)

(73) Assignee: SingLi Technology Inc., JhongHe, Taipei County (TW)

( * ) Notice: Subject to any disclaimer, the term of this patent is extended or adjusted under 35 U.S.C. 154(b) by 309 days.

(21) Appl. No.: 12/588,775

(22) Filed: Oct. 28, 2009

(65) Prior Publication Data

US 2011/0037586 A1 Feb. 17, 2011

(30) Foreign Application Priority Data

Aug. 13, 2009 (TW) .............................. 98127229 A

(51) Int. Cl.
  *G08B 1/08* (2006.01)
(52) U.S. Cl. .............. 340/539.1; 340/539.11; 340/573.1; 340/506; 340/3.1; 340/539.12
(58) Field of Classification Search ............... 340/539.1, 340/539.11, 539.12, 506, 573.1
  See application file for complete search history.

(56) References Cited

U.S. PATENT DOCUMENTS

| | | | |
|---|---|---|---|
| 5,455,851 A * | 10/1995 | Chaco et al. | 379/38 |
| 2006/0111939 A1 * | 5/2006 | Bixler et al. | 705/2 |
| 2006/0155584 A1 * | 7/2006 | Aggarwal | 705/3 |
| 2010/0318378 A1 * | 12/2010 | Auker et al. | 705/2 |

* cited by examiner

*Primary Examiner* — Daryl Pope
(74) *Attorney, Agent, or Firm* — Bacon & Thomas, PLLC

(57) ABSTRACT

In a mistake-proof monitoring method applied to a bedridden care system, the bedridden care system includes a computer, a plurality of transmitters and a warning device. The computer will generate a shutdown message to notice a nurse to check whether the transmitter is shut down maliciously, if no sensing message is transmitted from any transmitter within a predetermined time or a predetermined number of times. The computer will generate a detachment message to the warning device, if the transmitter is contacted improperly with a sensor. The computer will generate an error message to the warning device, if the time interval between the current time and a previous time occurring an abnormal situation is beyond a predetermined normal time interval and the sensor is not installed at a correct detected position. The mistake-proof monitoring method can immediately discover whether or not the sensors or the transmitters are operated at normal conditions.

11 Claims, 3 Drawing Sheets

MISTAKE-PROOF MONITORING METHOD OF BEDRIDDEN CARE SYSTEM

FIELD OF THE INVENTION

The present invention relates to a bedridden care system, in particular to a mistake-proof monitoring method that monitors whether or not the bedridden care system is operated at normal conditions by analyzing data transmitted from the bedridden care system to prevent a failure of providing nursing care services to patients timely due to human mistakes or operating errors.

BACKGROUND OF THE INVENTION

As medical technologies advance, our average life becomes increasingly longer, and ageing population tends to increase substantially. To cope with the required medical technology and social security system caused by the ageing population, a variety of medical teams, academic circles and related manufacturers are actively conducting researches, developments and promotions to establish healthcare systems to overcome various healthcare problems of elderly people and patients.

In general, elderly people have difficulty moving around and respond less promptly than they were young; consequently, elderly people usually need other's help on daily routines. For example, when elderly patients have urinary incontinence problem, they generally have to wear diapers so as to avoid their pants and bed sheets from being wetted easily by their urine, and most of them have to change their diapers frequently. However, due to limited mobile abilities, it is a hassle for the elderly people to change their own diapers. Actions such as undressing and re-dressing themselves before and after changing diapers require the elderly people to shift the center of gravity of their bodies. During the aforementioned process, the elderly person has to hold on an object (such as a table or a wall) to maintain balance. Undoubtedly, it is a dangerous task for the elderly people to change their own diapers, however, in the current society, double-income families are becoming very popular, couples are working and unable to take care of the elderly people in their families at home all the time, and thus increasingly more elderly people choose to live in a nursing home or a nursing center in order to get helps from nurses or care givers.

Since the nurses or care givers at nursing homes and/or care facilities have to go through professional trainings and be licensed in order to execute the associated nursing care works, increased expenses and insufficient care givers are always the problems many nursing homes and care facilities face today. Furthermore, in many nursing homes and care facilities, care givers are generally responsible for taking care of the daily living and hygiene of several patients (such as elderly people or mid to severe bedridden patients); therefore, the care givers are unable to accompany the elderly patients at all the time; resulting in infrequent change of diapers. If patients get illed (such as having a stroke or a psychoneurotic disorder), they may be unclear in speaking, unconscious or slow in response and unable to immediately notify the care givers to change their diapers, and other conditions (such as diaper rash or skin infection, etc) may occur easily if their diapers have not been changed for a long time, so that the patients will feel uncomfortable. To overcome the aforementioned problems, nursing homes and care facilities usually adopt a bedridden care system with a remote transmission function, such that when a patient needs assistance, the system can notify the care givers immediately. For instance, the nurse will install a sensor (such as a humidity sensor) at the patient's diaper first, and the sensor will transmit a detection signal to the care giver's computer through a wireless network, so that the care giver can learn about the patient's current conditions (such as having a wet diaper) and take necessary action (such as changing the diaper) immediately and effectively improve the patient's personal hygiene and comfort.

However, the currently existing bedridden care systems still have the following drawbacks. Firstly, most systems today only issue a warning whenever the computer receives an abnormal detection signal (such as a high humidity) transmitted from the sensor. If the nurse has not installed the sensor properly, or the sensor is malfunctioned, the sensor will be unable to provide a correct detection signal, and the computer will not provide the accurate information. As a result, the care givers will be unable to provide necessary assistance or immediate action to the elderly people or patients. In addition, since care givers are generally loaded with works and have different level of work ethics, they may not take necessary caring action (such as changing a diaper) immediately and properly after the computer has received the detection signal. If the care giver ignores the warning or is taking care of others, or turns off the sensor and wait for a period of time before changing the diaper for the elderly people or patients, the computer will not receive the correct information. If the patient is unable to express her/his conditions clearly or is unconscious, it will create many health problems and raise the issue of nursing negligence.

Therefore, it is an important subject for related manufacturers and nursing homes and care facilities to design products to assure that different situations can be detected to allow patients to receive timely care.

SUMMARY OF THE INVENTION

In view of the aforementioned shortcomings of the conventional bedridden care system that affects the benefits and rights of the elderly people or patients, the inventor of the present invention designed a mistake-proof monitoring method of a bedridden care system to overcome the shortcomings of the prior art and allow the elderly people and patients to have quick and effective care.

Therefore, the primary objective of the present invention is to provide a mistake-proof monitoring method applied to a bedridden care system, wherein the bedridden care system comprises of a computer, a plurality of transmitters and a warning device (such as a digital news ticker display), and the computer is coupled to the plurality of transmitters and the warning device for receiving messages from and transmitting messages to the transmitters and the warning device respectively, and the computer includes a healthcare database for storing device identification codes of all transmitters and healthcare data lists corresponding to the device identification codes, and each transmitter is coupled to a sensor for receiving a sensing message transmitted from the sensor, encoding the sensing message with the device identification code of the transmitter corresponding thereto, and then transmitting the sensing message to the computer, and the method comprises the following steps. The computer compares the device identification code encoded in the sensing message with the device identification code stored in the healthcare database and determines whether or not the sensing message transmitted from one of the transmitters has not been received for a predetermined time or in a predetermined number of times. If the sensing message transmitted from one of the transmitters has not been received for the predetermined time or in a predetermined number of times, then a shutdown message will be generated to the warning device to notice a nurse to check whether or not the transmitter is out of electric power or shut down maliciously, or else the computer will determine whether or not an ambient datum (such as a humidity, temperature or pressure reading) is detected in each sensing message. If the ambient datum is detected in each sensing message, then a detachment message will be generated to the warning device to notice the nurse to check whether or not a circuit between the transmitter and its corresponding sensor is connected improperly or fallen off, or else the computer will determine whether or not the detected ambient datum has a normal numeric value. If the detected ambient datum has the normal numeric value, then the computer will determine whether or not a time interval between the current time and a previous time occurring an abnormal situation is beyond a predetermined normal time interval (wherein the time interval for a patient with urinary incontinence is relatively constant, so that it indicates an abnormal condition if the time interval exceeds such constant time interval). If the time interval is beyond the predetermined normal time interval, then an error message will be generated to the warning device to notice the nurse to check whether or not the sensor is installed at a correct detected position. With this mistake-proof monitoring method, the present invention provides a quick way of finding out whether or not the sensors and the transmitters are operated at a normal working status to prevent human negligence or machine failure that may affect the benefits and rights of the elderly or patients.

DETAILED DESCRIPTION OF THE PREFERRED EMBODIMENTS

The present invention discloses a mistake-proof monitoring method of a bedridden care system for detecting the occurrence of a possible mistake or error of the bedridden care system, and issuing a corresponding warning according to different types of mistakes or errors to a nurse to take relevant actions. The method further records an error occurring time and an error eliminating time into a database for future reference in order to improve the patient care quality.

Figure 1:
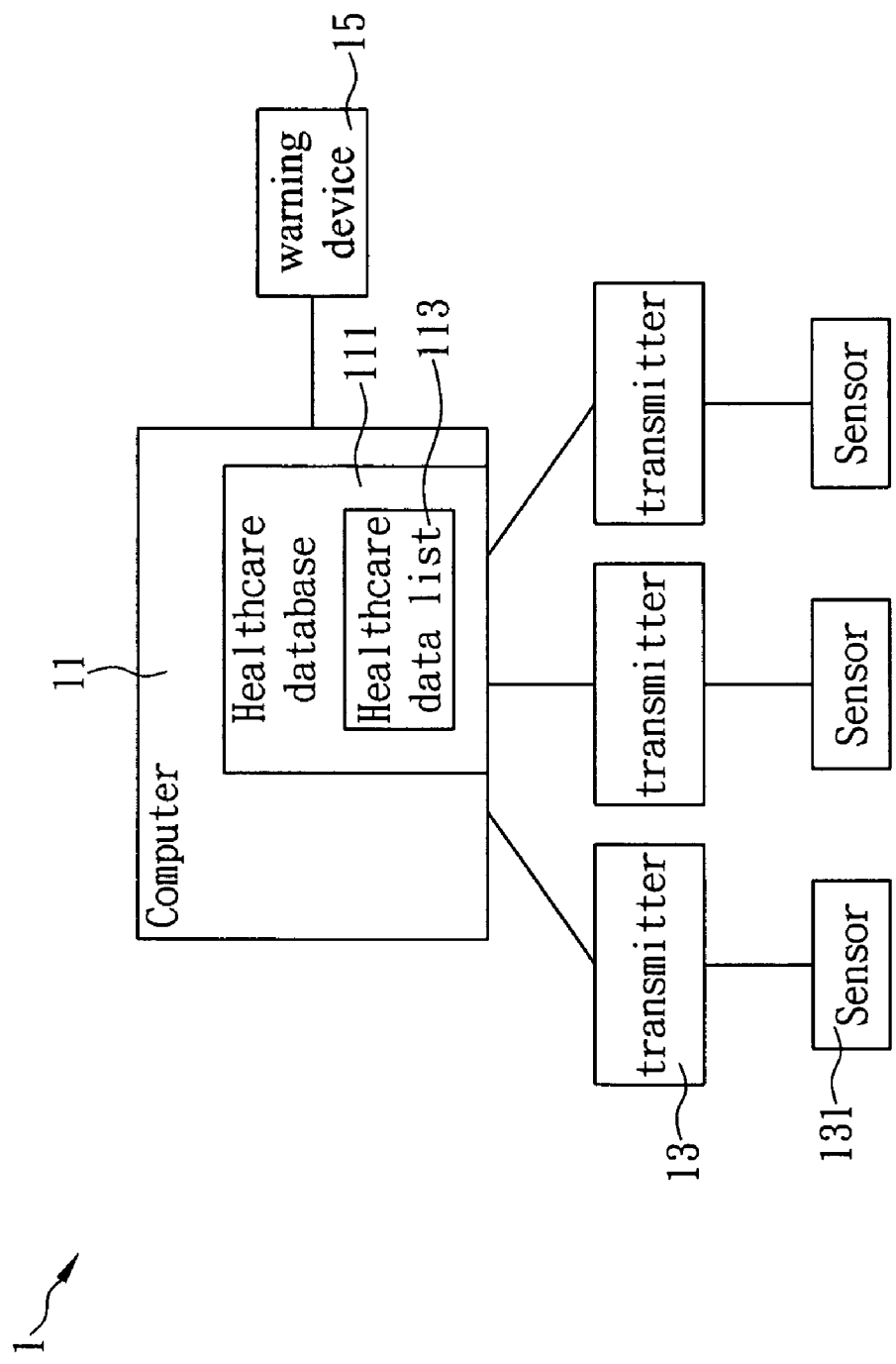
FIG. 1 is a block diagram of a bedridden care system of the present invention.

In a preferred embodiment of the present invention as shown in FIG. 1, the mistake-proof monitoring method is applied to a bedridden care system, wherein the bedridden care system 1 comprises a computer 11 (such as a personal computer or a server, etc), a plurality of transmitters 13 and a warning device 15 (such as a digital news ticker display, a speaker, an LED, a pager or a mobile phone, etc), and each transmitter 13 includes a device identification code, and the computer 11 is usually installed at a healthcare center or a medical care station and connected to each device such as the transmitter 13 and the warning device 15 through a cable or a wireless transmission for receiving and transmitting messages to each device. In this preferred embodiment, the computer 11 transmits data via a Zigbee wireless communication protocol, since the low-power Zigbee features a low power consumption and supports one-to-many transmissions, and thus the Zigbee protocol can be used in hospitals and clinics to avoid interfering the operation of other precision instruments. The computer 11 further includes a healthcare database 111 for storing device identification codes of all transmitters 13 and a plurality of healthcare data lists 113 corresponding to the device identification codes, wherein each healthcare data list 113 records related information (such as age, name, urination time, dosage, error occurring time, and error eliminating time, etc) of a care receiver (such as an elderly person or a patient), so that a supervisor of caretakers or a family member of a care receiver can review the healthcare data lists 113 to learn about the conditions of the care receiver in the past period of time and to check whether the care receiver is ignored, so as to improve the nursing quality for the care receivers.

In FIG. 1, each transmitter 13 is electrically coupled to a sensor 131, and the sensor 131 can detect the current ambient condition and transmit a predetermined time to the corresponding transmitter 13. For example, if a care receiver is an elderly patient with urinary incontinence, then the sensor 131 is a humidity detector installed onto a diaper, and the sensor 131 is set with a predetermined detection and message return time equal to 5 minutes, such that the sensor 131 will detect a current humidity of the diaper once every five minutes, and will transmit detection information to the transmitter 13. If the care receiver is an elderly person who takes sleeping pills on a regular basis, then the sensor 131 is a pressure sensor installed to a mattress, and the sensor 131 is set with a predetermine detection and message return time equal to one minute, such that the sensor 131 will detect a current pressure of the mattress once per minute and will transmit detection information to the transmitter 13, so that a nurse can change the type of sensors to fit different caring conditions. After the transmitter 13 has received the detection information transmitted from the sensor 131 and encoded the detection information with the device identification code, a sensing message is generated and transmitted to the computer 11. After the computer 11 has received the sensing message, the computer 11 reads ambient data in each sensing message to determine the condition of each sensor 131 and carries out the following procedure.

In FIG. 1, the computer 11 compares the device identification code encoded in the received sensing message with a device identification code stored in healthcare database 111 according to the preset time, and determines whether or not a sensing message transmitted from any one of the transmitters has not been received for a predetermined time (such as 10 minutes) or in a predetermined number of times (such as twice). It is noteworthy to point out that the predetermined time refers to a factory default setting for the time of not receiving a return message, and such time is different from the foregoing predetermined detection and message return time of the sensor. For example, a care center has installed a transmitter 13 of a humidity detector, wherein a sensing message is returned to the computer 11 once every 5 minutes (which is the predetermined detection and message return time), and the care center has set the time for the transmitter 13 of an installed pressure detector to return a sensing message to the computer 11 once per minute in order to control the current conditions of every care receiver precisely. If the computer 11 has not received a sensing message transmitted from one of the transmitters 13 (which has installed a humidity detector) for 10 minutes (which is the time of not receiving the return message), or the computer 11 has not received the sensing messages transmitted from one of the transmitters 13 when the computer should have received the sensing messages twice from the same transmitter 13, then it shows that the transmitter 13 is out of electric power, or the transmitter 13 is turned off intentionally by the nurse, and thus the transmitter 13 cannot operate normally. Thus, the computer 11 will generate a shutdown message to the warning device 15 (such as displaying a digital news ticker display that indicates the transmitter of a patient of a certain room number is not working normally), and the nurse stationed at the healthcare center can send people to check the condition of the transmitter 13, and the computer 11 will record the current time in the corresponding healthcare data list 113 according to the device identification code of the transmitter 13. After the transmitter 13 is back to its normal operation, the normal operation time will be recorded in the same healthcare data list 113, such that if the transmitter 13 is out of electric power, the nurse can replace the battery to resume the normal operation of the transmitter 13. If the transmitter 13 is turned off maliciously, the nurse can provide necessary services (such as changing a diaper) to the care receiver immediately, so as to avoid the care receiver from being unattended when an abnormal situation occurs, or waiting for a patrolling nurse to find out the abnormal situation. The aforementioned arrangement can maintain the benefits and rights of the care receivers. In addition, the healthcare data list 113 contains records of error occurring time and error eliminating time, such that a nursing home or center investigator can have a full understanding of the nursing work effectively.

In FIG. 1, after the computer 11 has received a sensing message normally, the computer 11 will determine whether an ambient datum (such as a humidity, temperature or pressure reading) in each sensing message is detected. For example, the sensing message transmitted from a transmitter 13 with an installed humidity detector should contain a detected humidity value. If no numeric value is detected, it shows that the sensor 131 (which is the humidity detector) is connected improperly with the transmitter 13, or a circuit between the sensor 131 and the transmitter 13 is disconnected, such that the sensor 131 is unable to transmit the detection information to the transmitter 13, and the sensing message transmitted from the transmitter 13 does not contain the detected ambient datum, so that the computer 11 will generate a detachment message to the warning device 15 (such as displaying a digital news ticker display that indicates a poor connection between the transmitter and the sensor of a patient at a certain room number), and the nurse stationed at the healthcare center can send people to check the connection between the transmitter 13 and the sensor 131, and the computer 11 will record the current time in the healthcare data list 113 of the corresponding device identification code and the device identification code of the transmitter 13 that transmits the corresponding ambient datum. After the sensing message transmitted from the transmitter 13 is back to normal (or the sensing message includes a detected ambient datum), the current time of the normal operation will be recorded into the same healthcare data list 113. After the computer 11 has read a detected ambient datum in the sensing message, the computer 11 will determine whether the numeric value of the detected ambient datum is normal; if not, then the computer 11 will generate an abnormality message to the warning device 15 (such as displaying a digital news ticker display that indicates the need of changing a diaper for a patient at a certain room number), or else the detected ambient datum is stored into the healthcare data list 113 of the corresponding device identification code, and compared with the detected ambient datum previously stored in the healthcare data list 113 of the corresponding device identification code to determine whether a time interval between the current time and a previous time occurring an abnormal situation is beyond a predetermined normal time interval (such as a too-high humidity). Since the time interval for patients with general urinary incontinence is a relatively constant time interval (such as two hours), therefore a too-long time interval (such as four hours) indicates that the sensor 131 is probably installed at a wrong position (such as a waist position of the diaper), so that the sensor 131 cannot detect the abnormal situation properly, but simply returns an abnormal sensing message, and the computer 11 will generate an error message to the warning device 15 (such as displaying a digital news ticker display that indicates the wrong installing position of the sensor of a patient at a certain room number) to notify the nurse to check whether the sensor 131 is installed at a correct detected position, and the computer 11 will record the current time into the healthcare data list 113 of the corresponding transmitter 13 until an abnormal sensing message transmitted from the transmitter 13 shows up, and then the computer 11 will record the current time into the same healthcare data list 113. With the mistake-proof monitoring method, the present invention can discover whether or not the sensor 131 and the transmitter 13 are operated at a normal working status to avoid the patient from failing to obtain healthcare services immediately and affecting the benefits and rights of the patients due to human negligence or machine failure.

Figure 2A:
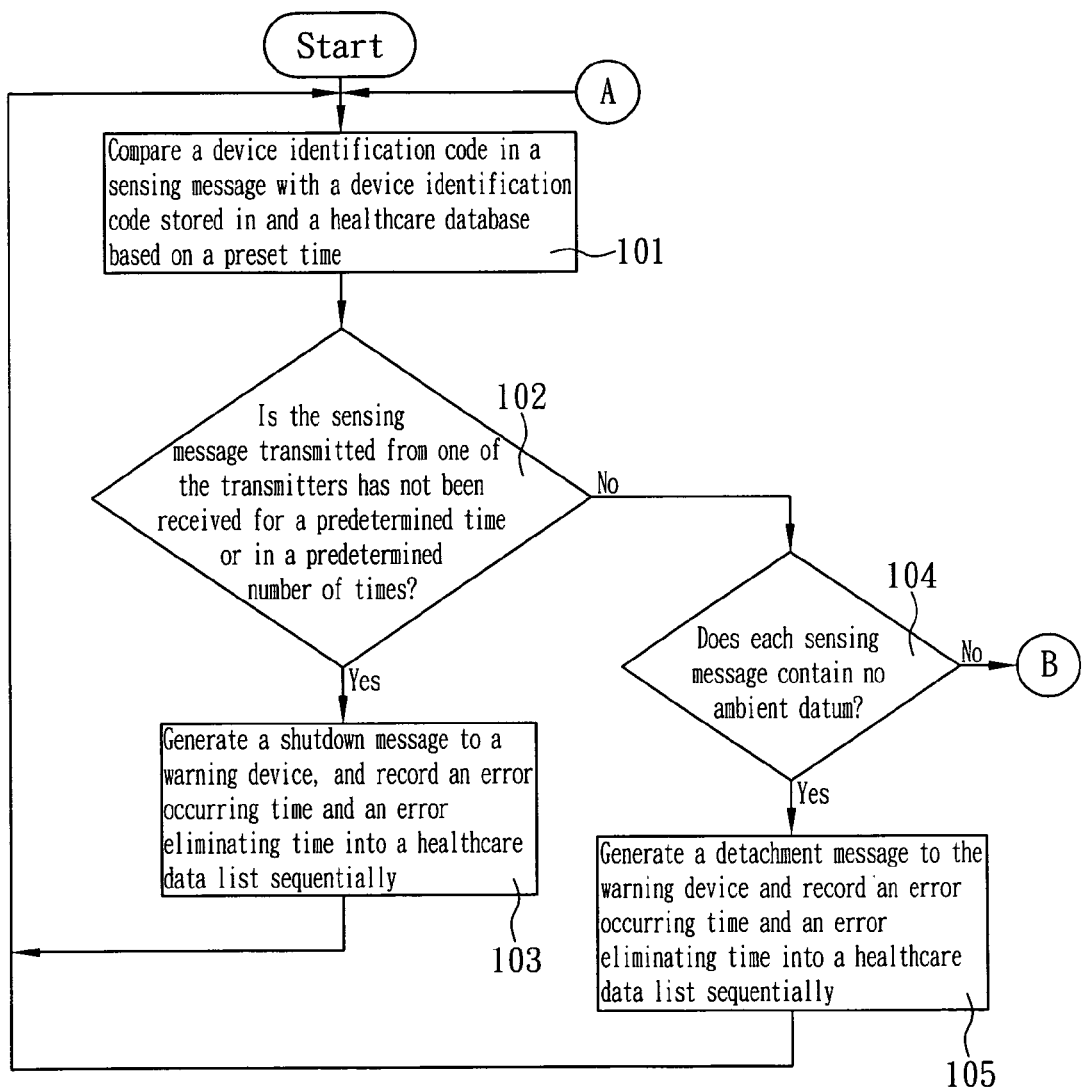
FIG. 2A is a flow chart of a mistake-proof monitoring method of the present invention.
Figure 2B:
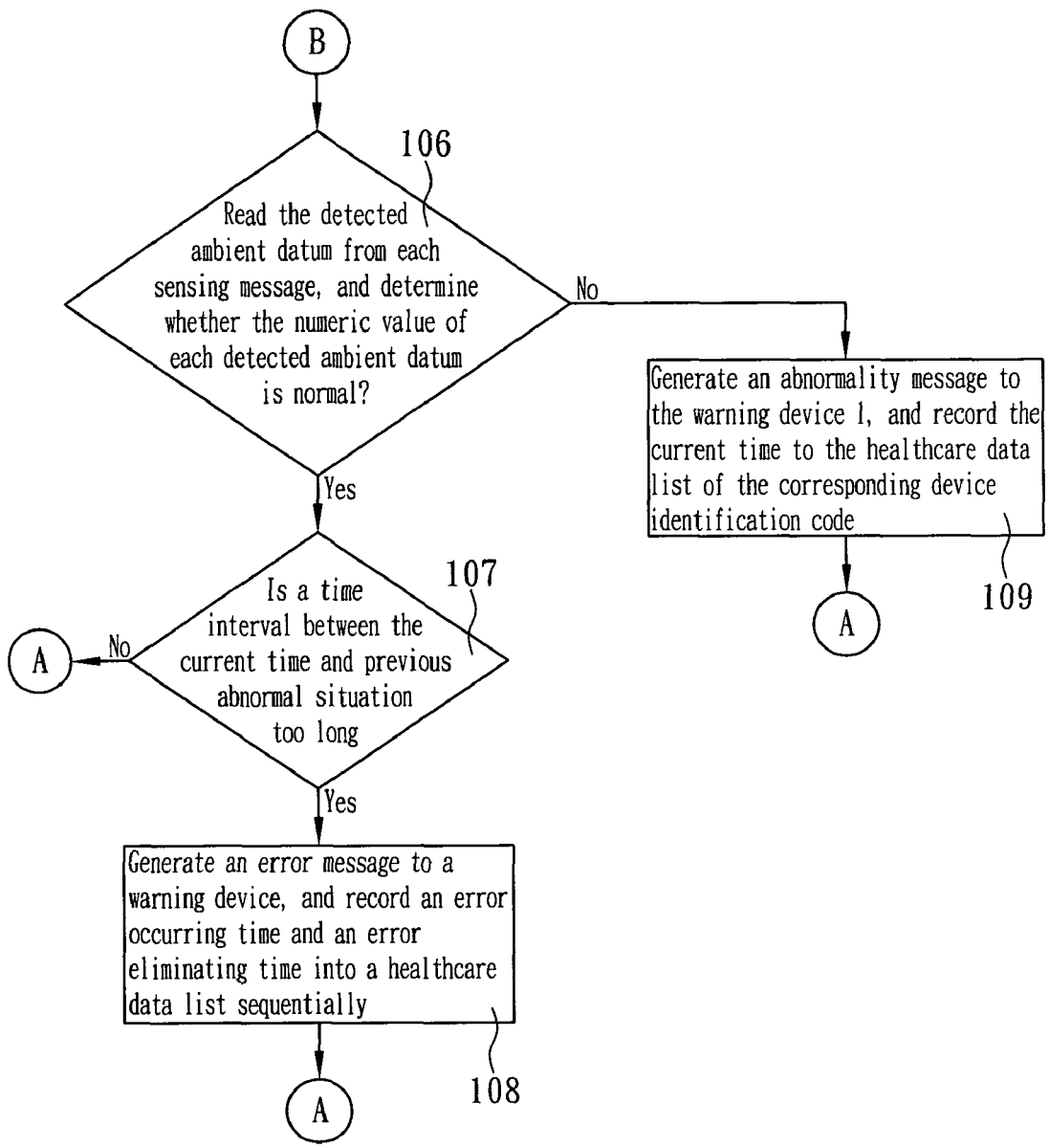
FIG. 2B is a continued flow chart of a mistake-proof monitoring method of the present invention.

To clearly disclose the method of the invention, the processing flow of the computer 11 as shown in FIGS. 1, 2A and 2B is described as follows:

Step (101): Compare a device identification code in a sensing message with a device identification code stored in and a healthcare database 111 according to a preset time, and then go to Step (102).

Step (102): Determine whether the sensing message transmitted from one of the transmitters 13 has not been received for a predetermined time or in a predetermined number of times; if yes, then go to Step (103), or else go to Step (104).

Step (103): Generate a shutdown message to the warning device 15, while recording the current time (which is the error occurring time) into a transmitter 13 of the corresponding device identification code that has not transmitted the sensing message, as well as recording the current time into a healthcare data list 113 of the corresponding device identification code until a sensing message returned from the transmitter 13 is received, and recording the return time (which is the error eliminating time) into the healthcare data list 113, and then go to Step (101).

Step (104): Determine whether an ambient datum in each sensing message is detected; if yes, go to Step (105), or else go to Step (106).

Step (105): Generate a detachment message to the warning device 15, while recording the current time (which is the error occurring time) into a healthcare data list 113 of the corresponding device identification code according to the device identification code of the transmitter 13 having no detected ambient datum, until the received sensing message returned from the transmitter 13 contains the detected ambient datum, as well as recording the return time (which is the error eliminating time) into the healthcare data list 113, and then go to Step (101);

Step (106): Read the detected ambient datum from each sensing message, and determine whether the numeric value of each detected ambient datum is normal; if yes, go to Step (107), or else go to Step (109).

Step (107): Save each detected ambient datum into the healthcare data list 113 of each corresponding device identification code, and compare the detected ambient datum with the detected ambient datum previously stored in the same healthcare data list 113, and determine whether a time interval between the current time and a previous time occurring an abnormal situation is beyond a predetermined normal time interval; if yes, then go to Step (108), or else go to Step (101).

Step (108): Generate an error message to the warning device 15, while recording the current time (which is the error occurring time) into a healthcare data list 113 of the corresponding device identification code according to the device identification code of the transmitter 13 having the too-long time interval, until the sensing message returned from the transmitter 13 contains the abnormal detected ambient datum, and recording a return time (which is the error eliminating time) into the corresponding healthcare data list 113, and then go to (101).

Step (109): Finally, generate an abnormality message to the warning device 15, while recording the current time into a healthcare data list 113 of the corresponding device identification code according to the device identification code of the transmitter 13 having an abnormal numeric value of the detected ambient datum, and then go to Step (101).

To clearly describe the aforementioned technical characteristics, an example of a care receiver A who is an elderly person having a sleeping problem and taking sleeping pills on a regular basis is used for illustrating the invention. A sensor (which is a pressure sensor in this embodiment) is installed to a mattress. In FIGS. 1, 2A and 2B, the computer 11 compares the device identification codes of all received sensing message with the device identification codes stored in the healthcare database 111 to find out whether there is any transmitter 13 that has not sent the sensing message. If the computer 11 determines that the transmitter 13 corresponding to the care receiver A has not sent out the sensing message, then a warning will be issued by the warning device 15, so that the nurse can check whether or not the care receiver A still lies on the mattress, and can also check whether or not the transmitter 13 is broken down or turned off. After the computer 11 has received the sensing message transmitted from the transmitter 13 of the care receiver A, the computer 11 will read the device identification code in the sensing message and the detected ambient datum. If the sensing message does not contain the detected ambient datum, the computer 11 will issue a warning from the warning device 15, so that the nurse can check whether or not the care receiver A still lies on the mattress and can also check whether or not a circuit between the transmitter 13 and the sensor 131 has a problem (such as falling apart or having a poor contact). After the computer 11 has read the detected ambient datum of the care receiver A, the computer will determine whether or not the detected ambient datum is normal. In this embodiment, if the care receiver A lies on the mattress, the detected ambient datum having a numeric value of 0 will be sent, and if the care receiver A leaves the mattress, then the detected ambient datum having a numeric value of 1 will be sent, so that after the care receiver A leaves the mattress, the computer 11 will read the detected ambient datum having the numeric value of 1. Since the care receiver A takes sleeping pills on a regular basis, therefore the care receiver A may fall asleep and lie at any place (such as a toilet). Now, the computer 11 compares whether or not the time of the care receiver A leaving the mattress exceeds a predetermined time; if yes, then the computer 11 will issue a warning from the warning device 15, so that the nurse can locate the care receiver A. If the care receiver A still lies on the mattress, then the sensor 131 may be installed at a wrong position and thus the sensor 131 cannot detect the pressure of the mattress.

In summation of the description above, the mistake-proof monitoring method of the present invention can prevent the following mistakes or errors effectively:
1. The transmitter 13 is out of electric power or turned off maliciously.
2. The circuit between the transmitter 13 and the sensor 131 is fallen off or connected improperly.
3. The sensor 131 is not installed to a correct detected position.

Thus, a nursing home or care center investigator can monitor the working attitude of the nurses to avoid human negligence, and the mistake-proof monitoring method of the present invention can reduce the unattended time of the care receivers during an abnormal situation, so as to guarantee the quality of caring the care receivers.

In addition to the aforementioned determination steps, an actual practice of the present invention further comprises the foregoing processing steps to improve the applicability of the present invention. In FIGS. 1, 2A and 2B, the transmitter 13 further encodes the remaining voltage value of the battery into the transmitted message, such that when the computer 11 reads the corresponding message, the computer 11 will determine whether or not the voltage value is smaller than a predetermined voltage value; if yes, then a low voltage message will be generated to the warning device 15 (such as displaying a digital news ticker display showing that a patient in a certain room number requires to change the battery of the transmitter), so that the nurse can change the battery immediately to prevent the shutdown of the transmitter 13 due to an exhausted battery.

It is noteworthy to point out that the terminologies used in the preferred embodiment of the present invention are used for the purpose of illustrating the invention only, but not intended for limiting the invention. Although the preferred embodiments of the present invention are illustrated by the plurality of healthcare data lists for simplicity, yet people ordinarily skilled in the art can understand the objective and nature of the invention and base on the technical characteristics of the invention to integrate the plurality of healthcare data lists into one in actual practices without limiting the invention to the aforementioned hardware system or structure only. While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. A mistake-proof monitoring method applied to a bedridden care system, wherein the bedridden care system includes a computer, a plurality of transmitters and a warning device, each transmitter includes a device identification code, the computer is coupled to each transmitter and the warning device for receiving messages from and transmitting messages to each transmitter and the warning device respectively and has a healthcare database installed therein for storing the device identification codes of all transmitters and healthcare data lists corresponding to the device identification codes, and each transmitter is coupled to a sensor for receiving a sensing message transmitted from the sensor, encoding the device identification code of the transmitter into the sensing message and then transmitting the sensing message to the computer, the method comprising the steps of:

the computer comparing the device identification code encoded in the sensing message with the device identification code stored in the healthcare database, and determining whether or not the sensing message transmitted from one of the transmitter has not been received for a predetermined time or in a predetermined number of times;

the computer determining whether or not an ambient datum exists in the sensing message after the sensing message is received;

the computer reading the ambient datum existing in the sensing message, and then determining whether or not a numeric value of the ambient data is normal; and the computer determining whether or not a time interval between a current time and a previous time occurring an abnormal situation is beyond a predetermined normal time interval, when the numeric value of the ambient datum is normal.

2. The mistake-proof monitoring method of claim 1, wherein the computer will generate a shutdown message to the warning device, when the computer determines that the sensing message transmitted from one of the transmitters has not been received within the predetermined time or in the predetermined number of times.

3. The mistake-proof monitoring method of claim 1, wherein the computer will generate a detachment message to the warning device, when the computer determines that no ambient datum exists in the sensing message.

4. The mistake-proof monitoring method of claim 1, wherein the computer will generate an abnormality message to the warning device, when the computer determines that a numeric value of the detected ambient datum is abnormal.

5. The mistake-proof monitoring method of claim 1, wherein the computer will generate an error message to the warning device, when the time interval between the current time and the previous time occurring the abnormal situation is out of a predetermined time interval.

6. The mistake-proof monitoring method of claim 1, wherein the transmitter further encode a voltage value of the transmitter into the sensing message, such that when the computer reads the sensing message, the computer will determine whether or not the voltage value is lower than a predetermined voltage value.

7. The mistake-proof monitoring method of claim 6, wherein the computer will generate a low voltage message to the warning device, when the computer determines that the voltage is less than a predetermined voltage value.

8. The mistake-proof monitoring method of claim 2, wherein the computer further records a time of issuing each of the messages into the healthcare data list corresponding to the device identification code of the transmitter, and also records a time of correcting each situations corresponding to the messages into the healthcare data list corresponding to the device identification code of the transmitter.

9. The mistake-proof monitoring method of claim 3, wherein the computer further records a time of issuing each of the messages into the healthcare data list corresponding to the device identification code of the transmitter, and also records a time of correcting each situations corresponding to the messages into the healthcare data list corresponding to the device identification code of the transmitter.

10. The mistake-proof monitoring method of claim 4, wherein the computer further records a time of issuing each of the messages into the healthcare data list corresponding to the device identification code of the transmitter, and also records a time of correcting each situations corresponding to the messages into the healthcare data list corresponding to the device identification code of the transmitter.

11. The mistake-proof monitoring method of claim 5, wherein the computer further records a time of issuing each of the messages into the healthcare data list corresponding to the device identification code of the transmitter, and also records a time of correcting each situations corresponding to the messages into the healthcare data list corresponding to the device identification code of the transmitter.

* * * * *